(12) United States Patent  
Berthusen et al.

(10) Patent No.: US 8,052,690 B2  
(45) Date of Patent: *Nov. 8, 2011

(54) VARIABLE ANGLE ORTHOPAEDIC REAMER DRIVER

(75) Inventors: Andrew Hans Berthusen, Warsaw, IN (US); Bryan Mendenhall, Claypool, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 219 days.

This patent is subject to a terminal disclaimer.

(21) Appl. No.: 12/362,922

(22) Filed: Jan. 30, 2009

(65) Prior Publication Data

US 2009/0138016 A1    May 28, 2009

Related U.S. Application Data

(63) Continuation of application No. 11/033,603, filed on Jan. 12, 2005, now Pat. No. 7,503,921.

(60) Provisional application No. 60/536,156, filed on Jan. 13, 2004.

(51) Int. Cl.  
*A61B 17/00*    (2006.01)

(52) U.S. Cl. ........................................................ 606/81  
(58) Field of Classification Search ............... 606/79–81  
See application file for complete search history.

(56) References Cited

U.S. PATENT DOCUMENTS

| 1,102,863 | A | 7/1914 | Bojas |
| 1,395,436 | A | 11/1921 | Lawrence |
| 1,398,234 | A | 11/1921 | Landis |
| 2,794,357 | A | 6/1957 | Lykins, Jr. |
| 5,236,289 | A | 8/1993 | Salyer |
| 5,409,332 | A | 4/1995 | Chabot, Jr. et al. |
| 6,105,473 | A | 8/2000 | Huang |

*Primary Examiner* — Nicholas Woodall  
(74) *Attorney, Agent, or Firm* — Taylor IP, P.C.

(57) ABSTRACT

An orthopaedic reamer driver includes a tubular housing having at least one first positioning feature. A driveshaft within the housing has a drive end. A variable angle cap is pivotally coupled with the housing adjacent the drive end. The variable angle cap includes at least one leg extending along a side of the housing. Each leg has a second positioning feature selectively engaging and disengaging with a corresponding first positioning feature at a selected one of a plurality of angular positions. Each second positioning feature maintains the variable angle cap at the selected angular position when engaged with the corresponding first positioning feature. A variable angle joint is coupled to the drive end, and a reamer drive head is coupled to the variable angle joint.

5 Claims, 7 Drawing Sheets

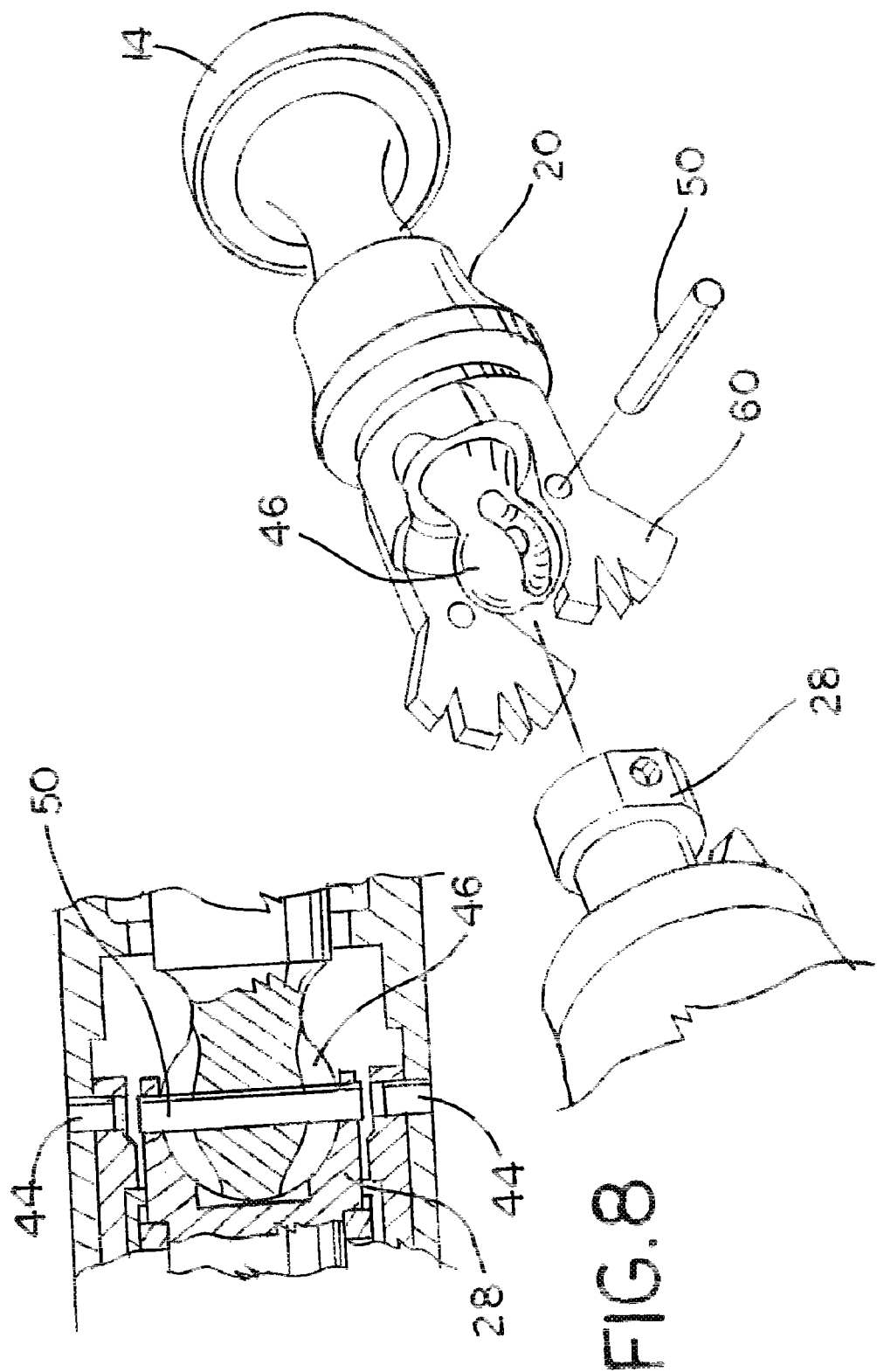

VARIABLE ANGLE ORTHOPAEDIC REAMER DRIVER

CROSS REFERENCE TO RELATED APPLICATIONS

This is a continuation of U.S. patent application Ser. No. 11/033,603 entitled VARIABLE ANGLE ORTHOPAEDIC REAMER DRIVER filed on Jan. 12, 2005, now U.S. Pat. No. 7,503,921 which is based on a U.S. provisional patent application Ser. No. 60/536,156, entitled "VARIABLE ANGLE DRIVER, filed Jan. 13, 2004.

BACKGROUND OF THE INVENTION

1. Field of the Invention

The present invention pertains generally to surgical instruments and, more particularly, to surgical instruments such as surgical tool drivers particularly suited for use in orthopaedic surgical procedures.

2. Description of the Related Art

An orthopaedic reamer assembly is used to cut a bone and thereby form the bone with a predetermined shape for receiving an orthopaedic implant. For example, an intramedullary reamer may be placed into the intramedullary canal of the bone and used to ream the interior of the bone to receive the stem of an orthopaedic implant. Such a reamer includes a radial, peripheral surface which generally includes a plurality of radially extending teeth for cutting the bone in a radial direction as the reamer proceeds in an axial direction into the bone. The size of the opening formed in the bone is determined by the outside diameter of the reamer.

An orthopaedic reamer assembly may also be used to shape an exterior surface of a bone. A rotary tool provides the motive force and is connected to a driver which is connected to the reamer. The driver generally has a shaft and a drive end. Reamers are typically hemispherical in shape and attach to the drive end at the base of the hemisphere. The distal face has a shape which corresponds to the shape of an orthopaedic implant to be received within the bone, and includes a plurality of cutting teeth extending from the distal face. The reamer is placed against the bone surface to be cut, such as an acetabulum or glenoid, and is plunge cut into the bone. Such reamers are effective for removing a portion of the bone so that the bone is shaped to receive the implant.

Minimally invasive surgery reduces the size of the incision site to in turn reduce trauma and recovery time for a patient. Orthopaedic reamers have been designed for minimally invasive surgery, e.g., U.S. patent application Ser. No. 10/659,812, assigned to the assignee of the present invention. A challenge with minimally invasive and certain other orthopaedic procedures is that it may be difficult to position the reamer at a desired angle relative to the bone surface to be cut. Orthopaedic reamer drivers are known which have a flexible shaft. The flexible shaft allows the reamer to travel along the path of a non-linear passage, such as an intramedullary canal, and thereby ream a non-linear opening. However, such a known driver having a flexible shaft cannot be held with the reamer positioned at a fixed acute angular orientation relative to the drive shaft since there is nothing to hold the reamer at that orientation during rotation.

What is needed in the art is an orthopaedic reamer driver which holds the reamer at a selected one of a plurality of angular orientations relative to the drive shaft while still allowing rotation of the reamer.

SUMMARY OF THE INVENTION

The present invention provides an orthopaedic reamer driver having a variable angle cap which may be fixed relative to the drive shaft at a selected one of a plurality of angular orientations.

The invention comprises, in one form thereof, an orthopaedic reamer driver, including a tubular housing having at least one first positioning feature. A driveshaft within the housing has a drive end. A variable angle cap is pivotally coupled with the housing adjacent the drive end. The variable angle cap includes at least one leg extending along a side of the housing. Each leg has a second positioning feature selectively engaging and disengaging with a corresponding first positioning feature at a selected one of a plurality of angular positions. Each second positioning feature maintains the variable angle cap at the selected angular position when engaged with the corresponding first positioning feature. A variable angle joint is coupled to the drive end, and a reamer drive head is coupled to the variable angle joint.

An advantage of the present invention is that the reamer may be oriented and fixed at variable angular orientations relative to the drive shaft.

Another advantage is that the angular orientations may be easily changed by sliding a collar and pivoting the reamer relative to the drive shaft.

Yet another advantage is that the particular type of variable angle joint interconnecting the drive shaft and reamer can vary depending on the application.

Still another advantage is that the fixed angular orientations can vary from one application to another by varying the position of the slots in the variable angle cap.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 7 is an exploded, perspective view of the drive end of the orthopaedic reamer assembly; and FIG. 8 is a fragmentary, sectional view of the drive end of the orthopaedic reamer assembly.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
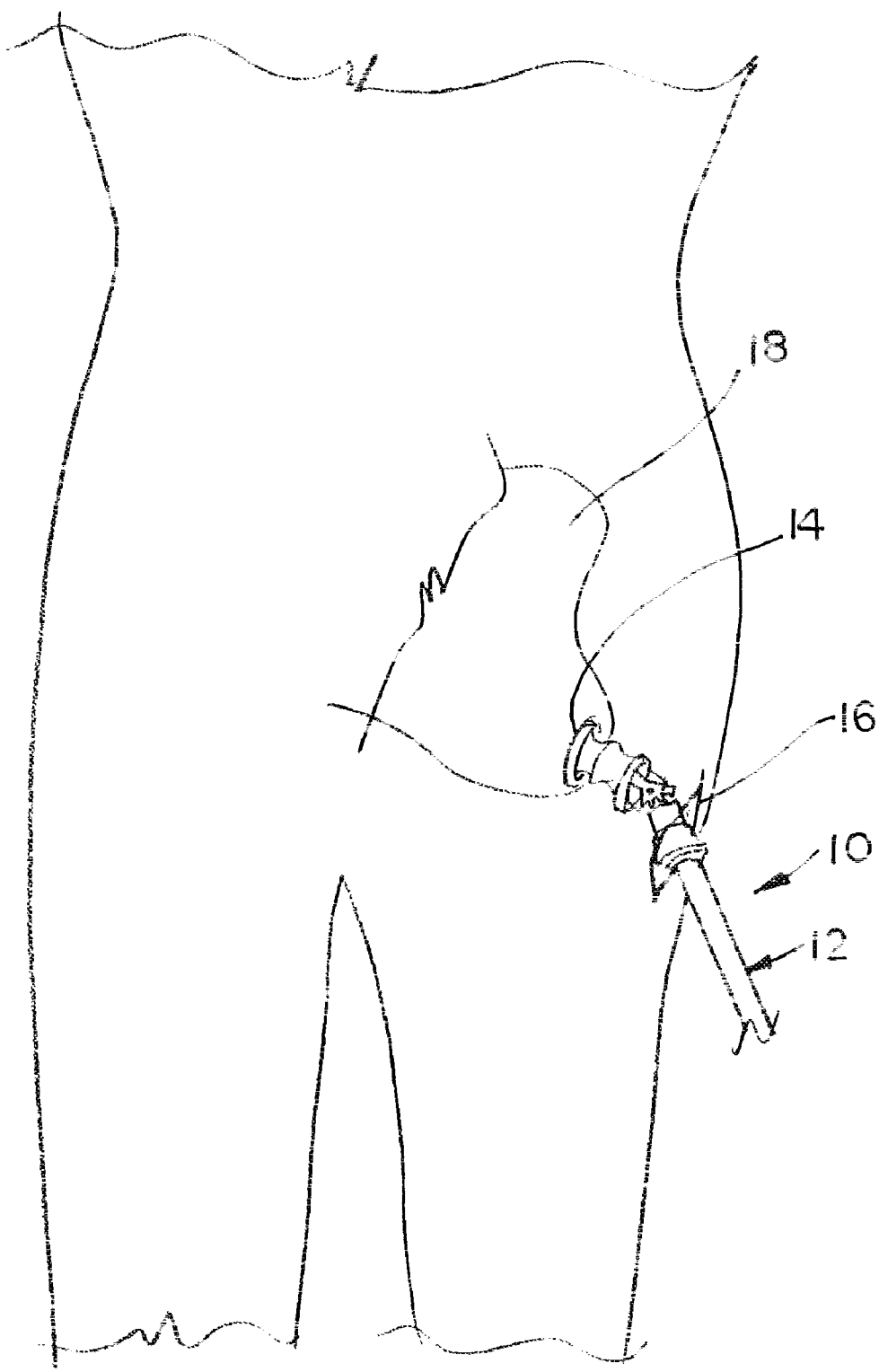
FIG. 1 is a simplified view of an orthopaedic reamer assembly including an embodiment of a reamer driver of the present invention, inserted in an incision for hip replacement surgery.

Referring now to the drawings, and, more particularly to FIG. 1, there is shown an embodiment of an orthopaedic reamer assembly 10 which includes a reamer driver 12 and a reamer 14. Reamer driver 12 extends through an incision 16 formed in a patient, and reamer 14 is shown relative to an acetabulum in a pelvic bone 18 within the patient. Orthopaedic reamer assembly 10 can be used for other applications, such as forming a glenoid in a shoulder.

Figure 2:
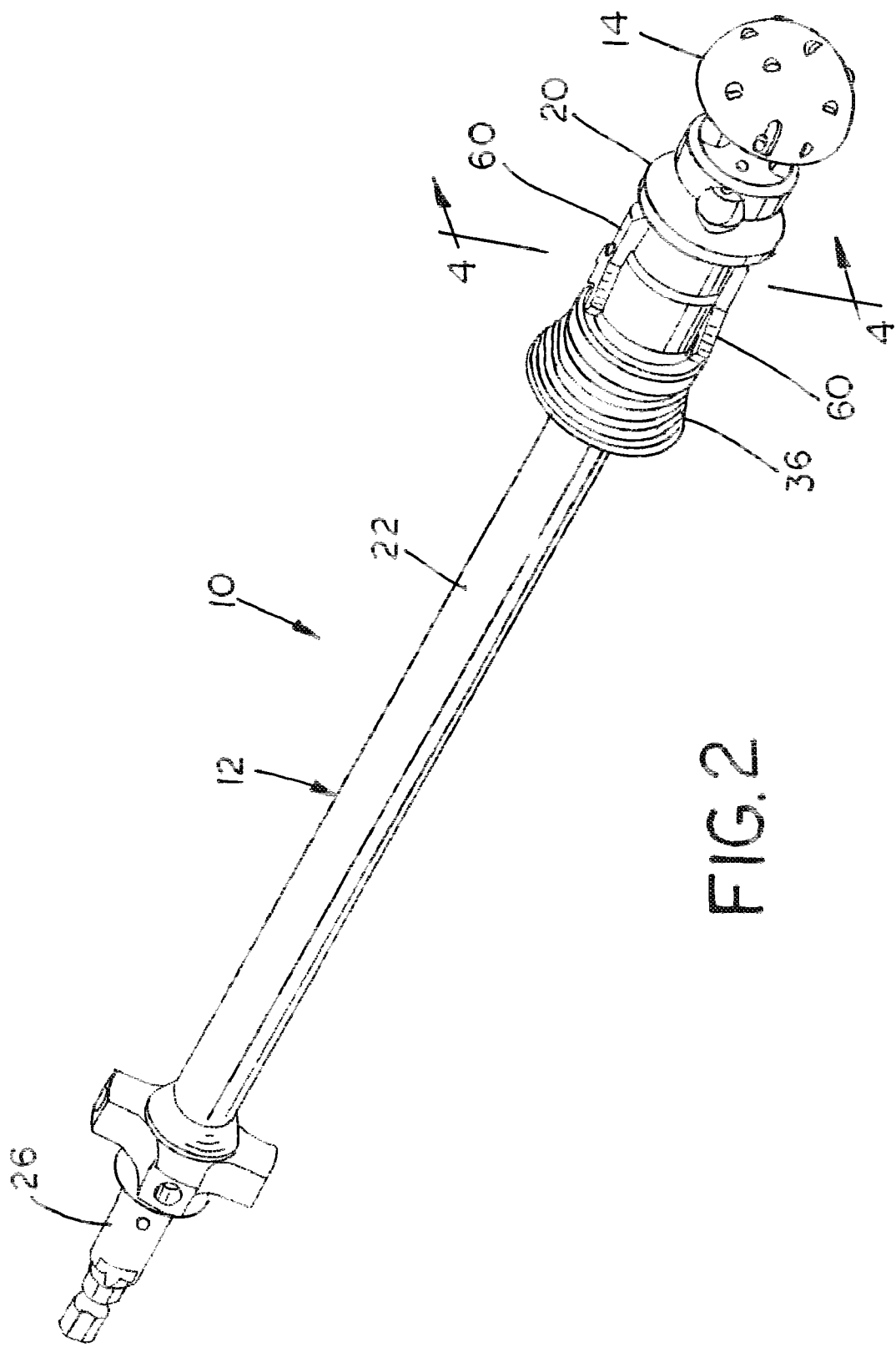
FIG. 2 is a perspective view of the orthopaedic reamer assembly shown in FIG. 1.
Figure 3:
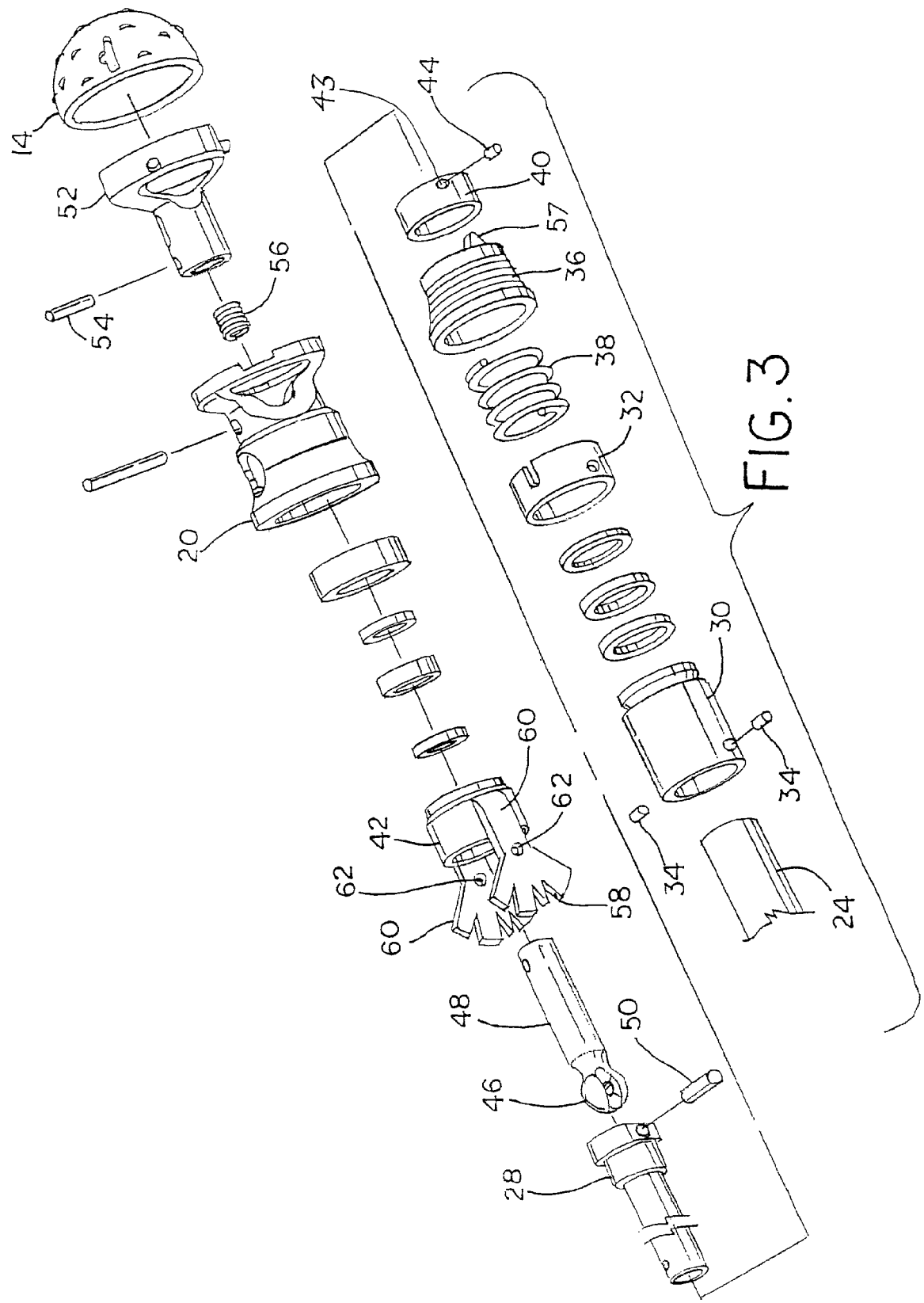
FIG. 3 is an exploded, perspective view of the orthopaedic reamer assembly shown in FIGS. 1 and 2.
Figure 4:
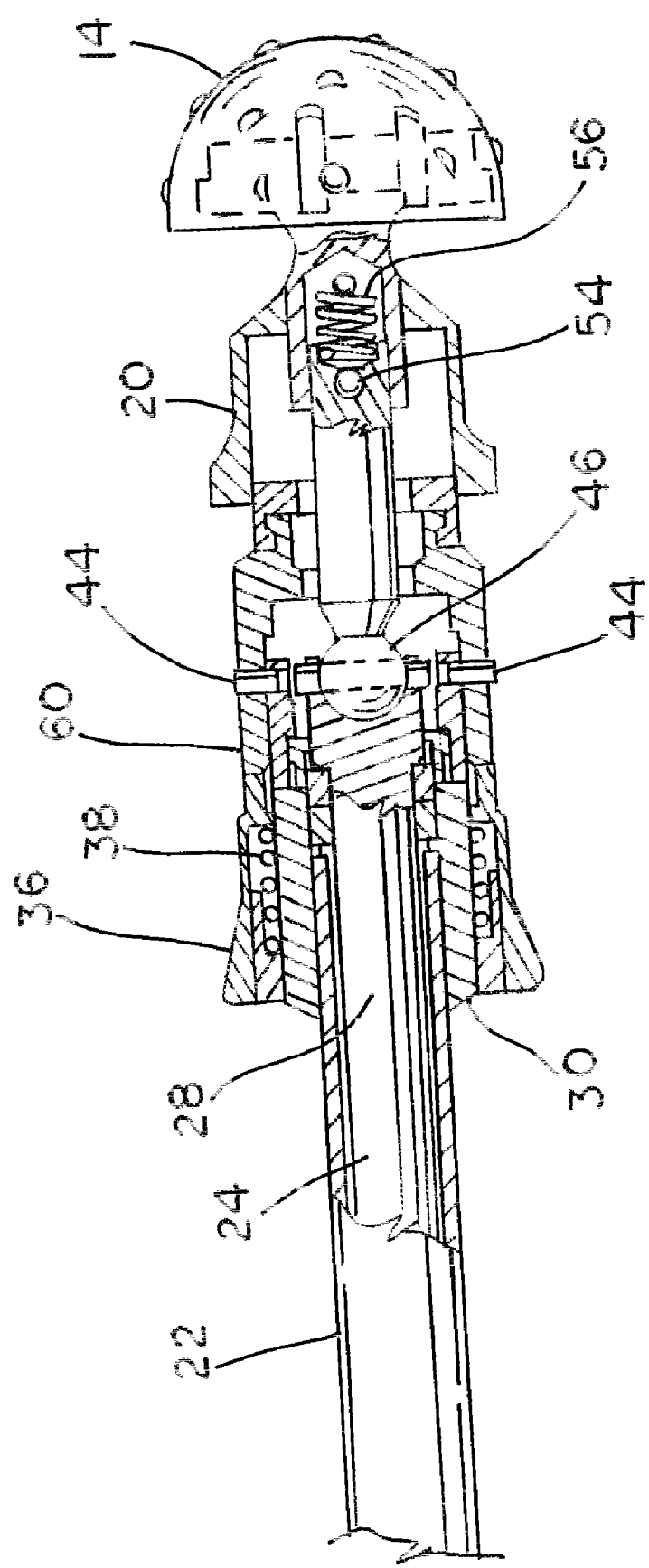
FIG. 4 is a fragmentary, sectional view taken along line 4-4 in FIG. 2.
Figure 5:
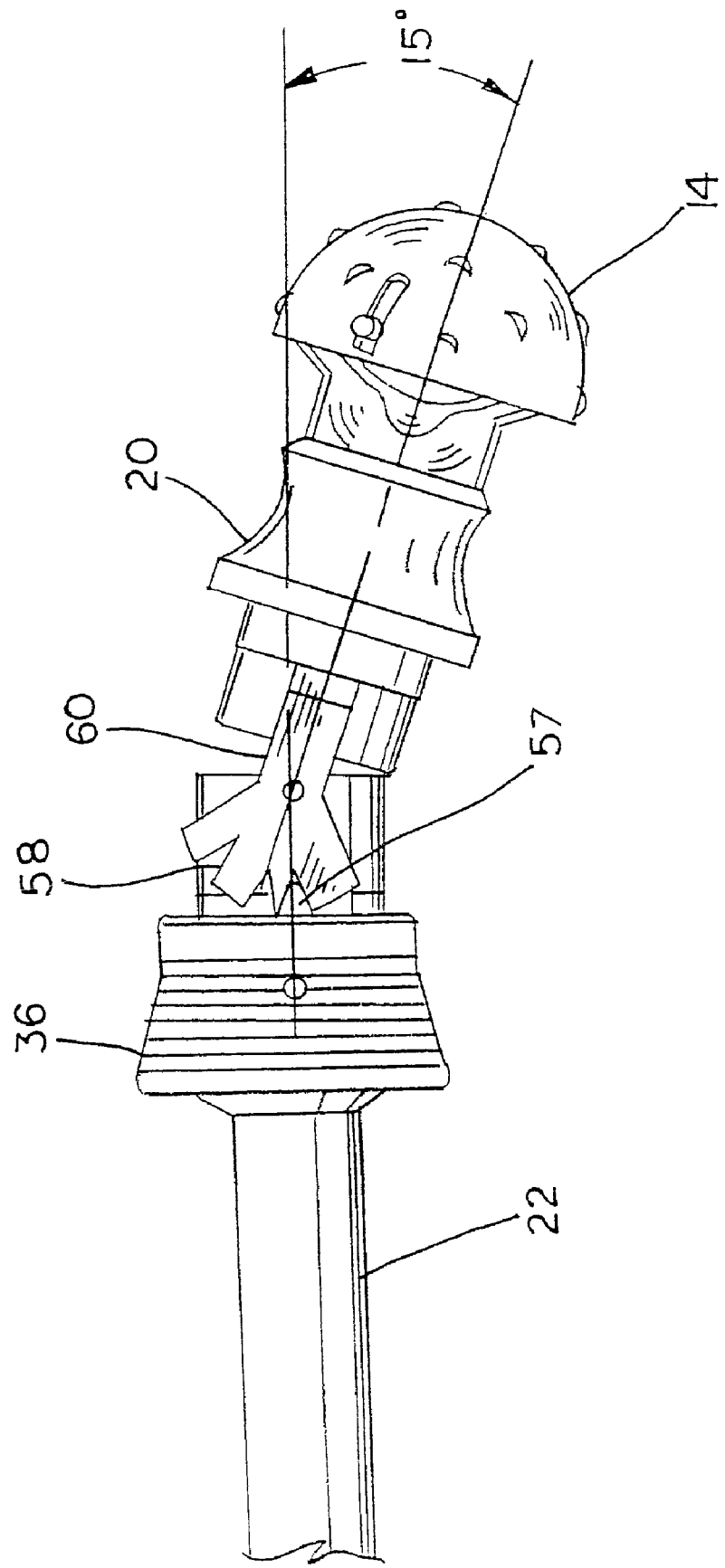
FIG. 5 is a side view of the orthopaedic reamer assembly shown in FIGS. 1-4, with the reamer oriented at a selected angular orientation.
Figure 6:
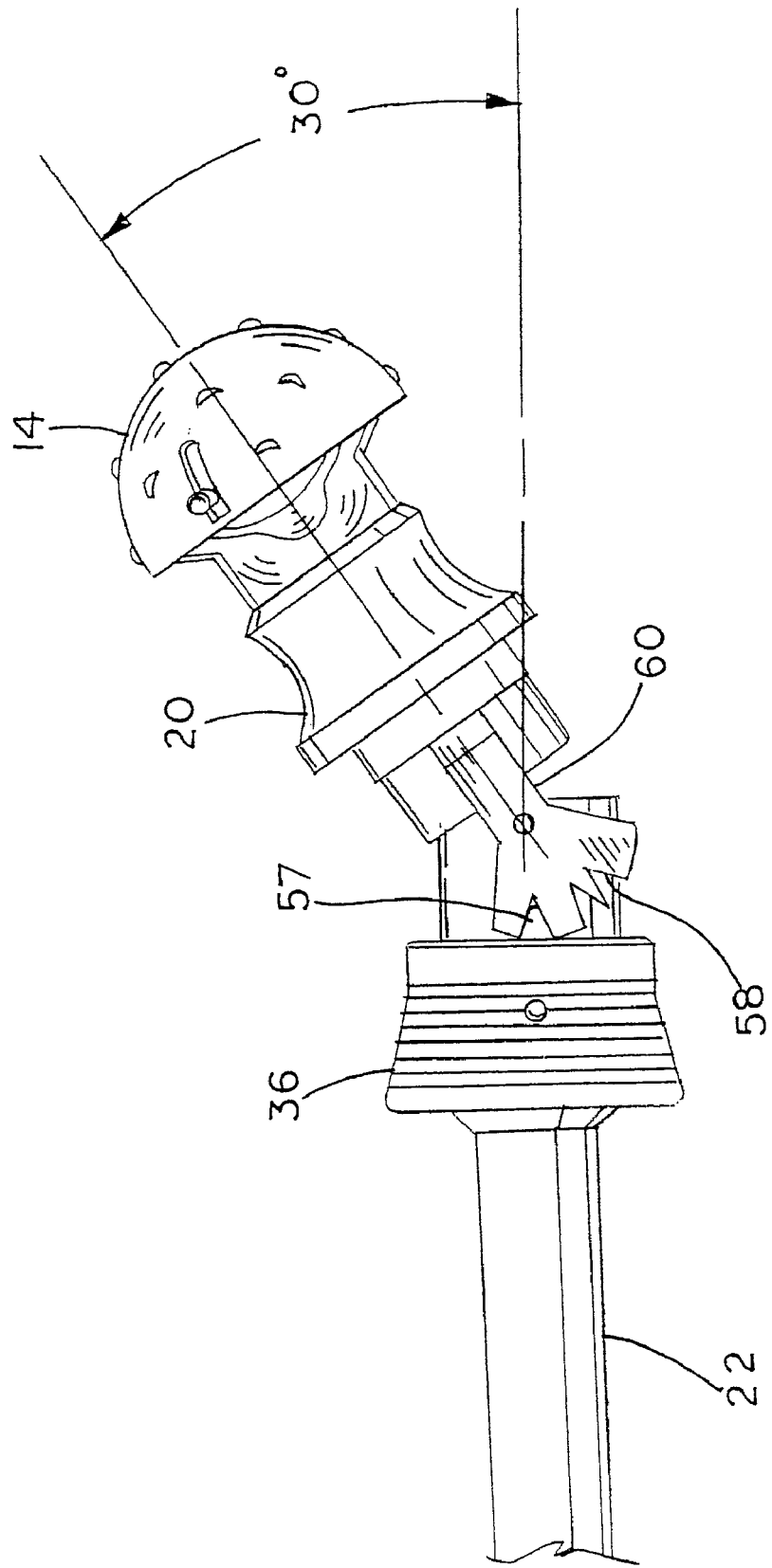
FIG. 6 is a side view of the orthopaedic reamer assembly shown in FIGS. 1-4, with the reamer oriented at another selected angular orientation.

Referring now to FIGS. 2-4, orthopaedic reamer assembly 10 is shown and will be described in greater detail. Reamer driver 12 is detachably coupled with reamer 14 by longitudinally sliding reamer release collar 20 and rotating reamer 14. When configured as an acetabular reamer, reamer 14 has a generally hemispherical shape with an outer surface defining a plurality of cutting teeth. The shape and number of cutting teeth can vary, depending on the application. Reamer driver 12 includes a tubular housing 22 through which a drive shaft 24 extends. Drive shaft 24 has a driven end 26 which is coupled with a rotary driver, such as a drill or the like (not shown). Drive shaft 24 also includes a drive end 28 which rotatably drives reamer 14 at a selected angular orientation, as will be described in more detail hereinafter.

Tubular housing 22 carries and is defined as including a fixed collar 30. A stop collar 32 is carried by fixed collar 30 and coupled therewith using a pair of pins 34. A release collar 36 is slidably positioned over each of fixed collar 30 and stop collar 32, and is biased in an axial direction toward reamer 14 using spring 38. Collar 40 also is coupled with and defines a portion of housing 22 adjacent the distal end of fixed collar 30. Collar 40 includes a pair of axially aligned holes 42 providing pivotal coupling with variable angle cap 42 through the use of a pair of short pivot pins 44.

Drive end 28 of drive shaft 24 includes a generally hemispherical socket (FIG. 4) which receives a generally spherical head 46 of a variable angled joint 48. Spherical head 46 is fastened to drive end 28 using pin 50 which passes through a transverse opening in head 46. Spherical head 46 also includes slot shaped openings allowing movement of variable angle joint 48 in multiple directions relative to drive end 28. Such a variable angled joint is disclosed, e.g., in U.S. Pat. No. 5,236,289 (Salyer), which is assigned to the assignee of the present invention and incorporated herein. Other types of variable angled joints, such as U-joints, flexible joints, etc. may also be used.

The distal end of variable angled joint 48 is coupled with drive head 52 using a pin 54. Spring 56 biases reamer release collar 20 toward reamer 14. When slid in a direction away from reamer 14, drive head 52 may be disengaged from reamer 14.

Release collar 36 includes a pair of V-shaped projections 56 on opposite sides of the distal face. When biased toward reamer 14, projections 56 engage a selected one of a plurality of V-shaped recesses 58 formed in the proximal end of legs 60 of variable angle cap 42. Legs 60 are positioned adjacent to collar 40, defining a part of housing 22, and are coupled with collar 40 using pins 44 which extend through axially aligned holes 62.

V-shaped recesses 58 may be formed at the proximal end of legs 60 so as to maintain a fixed angular orientation of variable angle joints 48 and reamer 14 relative to housing 22 and drive shaft 24. In the embodiment shown, recesses 58 are engaged with projections 56 at fixed angular orientations of 0, 15 and 30°, depending upon which recess is engaged. Of course, the number of recesses, angular orientation of the recesses, and shape of the recesses may vary, depending on the application.

When assembled, the axis of pins 44 and 50 are generally in alignment with each other such that variable angle cap 42 may be placed at a selected angular orientation, and variable angled joints 48 may move in multiple directions to allow rotation of drive shaft 24 and reamer 14.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer driver, comprising:
    a tubular housing including at least one first positioning feature;
    a drive shaft within said housing and having a drive end;
    a variable angle cap pivotally coupled with said housing adjacent said drive end, said variable angle cap including at least one leg extending along a side of said housing, each said leg having a second positioning feature selectively engaging and disengaging with a corresponding said first positioning feature at a selected one of a plurality of angular positions, each said second positioning feature maintaining said variable angle cap at said selected angular position when engaged with said corresponding first positioning feature, said first feature being constrained to engage and disengage said second feature in an axial direction relative to said tubular housing wherein said first positioning feature combines a V-shaped projection and said second positioning feature comprises a plurality of V-shaped recesses;
    a variable angle joint coupled to said drive end; and
    a reamer drive head coupled to said variable angle joint.

2. The orthopaedic reamer driver of claim 1, wherein said variable angle cap includes a pair of legs extending on opposing sides of said housing.

3. The orthopaedic reamer driver of claim 1, wherein said variable angle cap includes a pair of axially aligned holes, and said variable angle cap is pivotally coupled to said housing with a pair of pivot pins respectively extending through said pair of holes.

4. The orthopaedic reamer driver of claim 1, wherein said variable angle joint comprises a ball joint having a pivot axis extending substantially through said pair of pivot pins.

5. The orthopaedic reamer driver of claim 1, wherein said variable angle joint comprises one of a ball joint, a U joint and a flexible joint.

* * * * *